(12) United States Patent
Orr

(10) Patent No.: US 11,298,588 B2
(45) Date of Patent: Apr. 12, 2022

(54) THERAPY AND PHYSICAL TRAINING DEVICE

(71) Applicant: XR Health IL LTD, Tel Aviv (IL)

(72) Inventor: Eran Orr, Brookline, MA (US)

(73) Assignee: XR Health IL LTD, Tel Aviv (IL)

(*) Notice: Subject to any disclaimer, the term of this patent is extended or adjusted under 35 U.S.C. 154(b) by 24 days.

(21) Appl. No.: 17/020,330

(22) Filed: Sep. 14, 2020

(65) Prior Publication Data
US 2020/0406092 A1   Dec. 31, 2020

Related U.S. Application Data

(63) Continuation of application No. 16/067,480, filed as application No. PCT/IL2016/051391 on Dec. 28, 2016, now Pat. No. 10,773,122.
(Continued)

(30) Foreign Application Priority Data

Mar. 7, 2016 (IL) .......................................... 244468

(51) Int. Cl.
*A63B 23/025* (2006.01)
*A63B 71/06* (2006.01)
(Continued)

(52) U.S. Cl.
CPC ........ *A63B 23/025* (2013.01); *A63B 21/0442* (2013.01); *A63B 21/0557* (2013.01);
(Continued)

(58) Field of Classification Search
CPC .............. A63B 23/025; A63B 21/0442; A63B 21/0557; A63B 21/4005; A63B 21/4007;
(Continued)

(56) References Cited

U.S. PATENT DOCUMENTS

| 4,089,330 A | 5/1978 | Nicolosi et al. |
| 6,106,437 A | 8/2000 | Brooks |

(Continued)

FOREIGN PATENT DOCUMENTS

| CN | 101034308 A | 9/2007 |
| CN | 101778653 A | 7/2010 |

(Continued)

OTHER PUBLICATIONS

Extended European Search Report issued by the European Patent Office in corresponding Application No. EP 16881411 dated Jul. 24, 2019.
(Continued)

*Primary Examiner* — Andrew S Lo
(74) *Attorney, Agent, or Firm* — Foley Hoag LLP; Erik A. Huestis

(57) ABSTRACT

A therapy and physical training system, comprising one or more movement sensors each of which positioned on a corresponding body part of a user, a first computer on a processor of which an application is running and a head mounted housing which is configured with a display on which images generated by the first computer are visible to the user. The application is configured to receive inputs from each of the sensors or from a second computer in data communication with each of the sensors, the application also configured to generate, in response to a real-time disposition of each of the corresponding body parts during performance of an exercise related body movement, a virtual reality object viewable by the user, the object being indicative of an additional body movement to be made by the user in order to conform with a user-specific exercise program.

15 Claims, 15 Drawing Sheets

Related U.S. Application Data

(60) Provisional application No. 62/272,267, filed on Dec. 29, 2015.

(51) Int. Cl.

| | | |
|---|---|---|
| *G06F 3/01* | (2006.01) | |
| *A63B 21/00* | (2006.01) | |
| *A63F 13/212* | (2014.01) | |
| *A63B 21/04* | (2006.01) | |
| *A63B 21/055* | (2006.01) | |
| *G16H 20/30* | (2018.01) | |
| *G02B 27/01* | (2006.01) | |
| *A63B 23/00* | (2006.01) | |
| *A63B 21/072* | (2006.01) | |
| *G16H 40/63* | (2018.01) | |

(52) U.S. Cl.
CPC ...... *A63B 21/4003* (2015.10); *A63B 21/4005* (2015.10); *A63B 21/4007* (2015.10); *A63B 71/0622* (2013.01); *A63F 13/212* (2014.09); *G02B 27/0176* (2013.01); *G06F 3/011* (2013.01); *G16H 20/30* (2018.01); *A63B 21/00061* (2013.01); *A63B 21/00069* (2013.01); *A63B 21/0726* (2013.01); *A63B 2023/006* (2013.01); *A63B 2071/0666* (2013.01); *A63B 2220/20* (2013.01); *A63B 2220/40* (2013.01); *A63B 2220/803* (2013.01); *A63B 2220/89* (2013.01); *A63B 2225/50* (2013.01); *A63B 2230/06* (2013.01); *A63B 2230/10* (2013.01); *A63B 2230/60* (2013.01); *A63F 2300/8082* (2013.01); *G16H 40/63* (2018.01)

(58) Field of Classification Search
CPC ............ A63B 21/4003; A63B 2220/20; A63B 2023/006; A63B 21/00061; A63B 2230/06; A63B 2220/89; A63B 2230/60; A63B 2225/50; A63B 2230/10; A63B 21/0726; A63B 21/00069; A63B 2220/40; A63B 2220/803; A63B 71/0619–0622; A63B 2071/0636–0666; G02B 27/0176; G16H 20/30; G16H 40/63; A63F 13/212; A63F 2300/8082; G06F 3/011

See application file for complete search history.

(56) References Cited

U.S. PATENT DOCUMENTS

| | | |
|---|---|---|
| 7,189,192 B2 | 3/2007 | Edgeton |
| 8,679,037 B2 | 3/2014 | Sarig-Bahat |
| 10,209,779 B2 | 2/2019 | Roh et al. |
| 10,773,122 B2 | 9/2020 | Orr |
| 2004/0058780 A1 | 3/2004 | Edgeton |
| 2008/0319252 A1 | 12/2008 | Chapman et al. |
| 2011/0230792 A1 | 9/2011 | Sarig-Bahat |
| 2012/0136274 A1 | 5/2012 | Burdea et al. |
| 2012/0253241 A1 | 10/2012 | Levital et al. |
| 2013/0009853 A1 | 1/2013 | Hesselink et al. |
| 2015/0241969 A1 | 8/2015 | Elangovan et al. |
| 2016/0349509 A1 | 12/2016 | Lanier et al. |

FOREIGN PATENT DOCUMENTS

| | | |
|---|---|---|
| CN | 203074707 U | 7/2013 |
| CN | 103732297 A | 4/2014 |
| CN | 103977539 A | 8/2014 |
| CN | 203838407 U | 9/2014 |
| CN | 104107134 A | 10/2014 |
| WO | WO-2015/126182 A1 | 8/2015 |

OTHER PUBLICATIONS

International Preliminary Report on Patentability for International Application No. PCT/IL2016/051391 dated Jul. 3, 2018.
International Search Report and Written Opinion for International Application No. PCT/IL2016/051391 dated Apr. 5, 2017.
Treatment of Neck Pain Assisted by Virtual Reality Research in Australian Universities (http://world.people.com.en/n/2015/0323/c1002-26733372.html) (2015).
Wikipedia: "Samsung Gear VR," Retrieved from the Internet: https://en.wikipedia.org/w/index.php?title=Samsung_Gear_VR&oldid=692786831.

THERAPY AND PHYSICAL TRAINING DEVICE

CROSS-REFERENCE TO RELATED APPLICATIONS

This application is a continuation of U.S. application Ser. No. 16/067,480, filed on Jun. 29, 2018, which is a national stage application of International Application No. PCT/IL2016/051391, filed on Dec. 28, 2016, which claims the benefit of Israel Application No. 244468, filed on Mar. 7, 2016 and U.S. Provisional Application No. 62/272,267, filed on Dec. 29, 2015, each of which is hereby incorporated by reference in their entirety.

FIELD

The present invention relates to the field of therapy and physical training devices. More particularly, the invention relates to a virtual reality enhanced therapy and physical training device that promotes the rehabilitation and strengthening of muscles in the neck or in other parts of the body.

BACKGROUND

Many people suffer from neck pain or need to undergo neck exercises for numerous reasons. For example, people who have been involved in a motor vehicle accident or have suffered an injury while playing contact sports such as football are prone to develop a whiplash associated disorder (WAD), a condition resulting from an acceleration-deceleration mechanism or any other impact that may cause damage to the neck muscles or to neck structures. Approximately 4 million people are hospitalized annually in the United States alone for WAD, while nearly a quarter of them never fully recover. The cost for WAD injuries, including health and insurance claims, is over 100 billion USD per year.

The majority of people who suffer from non-specific neck pain (NSNP) may have experienced symptoms associated with WAD or have an undiagnosed cervical herniated disc. For this population, the recommended treatment regimen includes a variety of exercises promoting neck movement and other functional activity training, leading to improved rehabilitation.

Commonly these exercises may be carried out in the comfort of one's home. However, due to the monotonic nature of these exercises, or due to the associated pain, many people do not adhere to the recommended regimen and therefore the sensation of pain is not adequately alleviated. H. Bahat et al, "Cervical Kinematic Training with and without Interactive VR Training for Chronic Neck Pain-A Randomized Clinical Trial", Manual Therapy 20 (2015) 68-78, discloses a virtual reality (VR) device for use as a cervical kinematic assessment and training tool, whereby user attention is directed to an external stimulus rather than to the body movements. The hardware includes a head-mounted display with a three-dimensional motion tracker. Dynamic motion tracking data is analyzed with use of range of motion (ROM), velocity and accuracy modules to elicit cervical motion by the user's response to visual stimuli provided by an interactive 3D virtual environment. During a VR session, a virtual object is controlled by the user's head motion in the four directions of flexion, extension, right rotation and left rotation. A training session also involves a laser pointer that is mounted on the user's head in order to perform a head pursuit task. The drawback of such an arrangement is the need and cost of a dedicated VR system, making the training less accessible to people who need to recover from neck injury or to prevent potential injury to the neck.

Home training has several limitations. With no direct guidance from the clinician, the patient has no immediate feedback to confirm correct performance of required exercises. Also, lack of such guidance and supervision often leads to even lower adherence; current literature discusses the nature of low adherence to home training, suggesting that patients tend to disregard the importance of prescribed home training. Moreover, patients that suffer from chronic or other long-term conditions (such as those associated with WAD or NSNP) are even less inclined to perform recommended home training (J. Kirsten et al, "Barriers to Treatment Adherence in Physiotherapy Outpatient Clinics: A Systematic Review", Man Ther. June, 2010; 15(32):220-228). As a result, the pain of an initial sensed condition may persist or even worsen—leading to other required medical interventions that could have been prevented, thus also increasing associated costs of the initial condition ("Adherence to Long-Term Therapies: Evidence for Action", World Health Organization, Geneva, Switzerland, 2003). The activation of muscles supporting the skeletal posture is an effective way to prevent many injuries as disclosed for example, in "Cervical Resistance Training-Effects on Isometric and Dynamic Strength" (Taylor et al., Aviation, Space, and Environmental Mechcine, Vol. 77, No. 11, November 2006).

It is an object of the present invention to provide a neck therapy and physical training device that facilitates neck mobility restoration, encourages conformance to an exercise regimen, and is cost effective.

It is another object of the present invention to provide a therapy and physical training device that facilitates rehabilitation and improved conditioning of a given body part.

Other objects and advantages of the invention will become apparent as the description proceeds.

BRIEF SUMMARY

The present invention provides a neck therapy and physical training device, comprising a head harness and one or more resistance applying elements which are attached to selected regions of said head harness, said one or more elements configured to provide a user-selected and location-specific level of resistance to a desired head movement that promotes neck muscle activity for a specific neck related condition.

The head harness is preferably configured with a plurality of spaced head engageable straps, each of said straps being provided with at least one of the regions that is coupleable with a resistance applying element, the coupled resistance applying element adapted to tension a neck related muscle that is located oppositely thereto and to force said tensioned muscle to contract until the head achieves a balanced condition. As referred to herein, the term "located oppositely thereto" means the relative geometric location of a neck related muscle or a group of muscles with respect to the coupled resistance applying element, prior to head movement, such that said neck related muscle or group of muscles coincides with or is connected to tissue located on a line extending from the resistance applying element through the head-related center of rotation while said head-related center of rotation is interposed between said tissue and said resistance applying element. When the muscle or group of muscles is tensioned by two contralaterally located resistance applying elements which may be bilaterally symmetrical to each other, the tissue coinciding with or connected to the muscle or group of muscles is located on a line medially extending between the two resistance applying elements and passing through the head-related center of rotation.

In one embodiment, the neck therapy device further comprises a head mounted display connected to the head harness on which is viewable computer generated images, thereby allowing neck rehabilitation training in conjunction with virtual reality enhancement.

The head mounted display may be configured with image forming lenses and with a slot in which is insertable a processor enabled device, such as a smartphone.

The present invention is also directed to a system comprising the neck therapy device, a computer configured to generate said images, a sensor in data communication with said computer for detecting, when the head harness is bodily engaged, a real-time three-dimensional disposition of the head of the user, and an application running on a processor of said computer.

Said application is configured to receive inputs from said sensor and to generate, in response to said real-time disposition, a virtual reality object viewable by the user on said display, said object being indicative of an additional head movement to be made by the user in order to conform to a user-specific exercise program.

The present invention is also directed to a therapy and physical training system, comprising one or more movement sensors each of which positioned on a corresponding body part of a user, a first computer on a processor of which an application is running, and a head mounted housing which is configured with a display on which images generated by said first computer are visible to said user.

Said application is configured to receive inputs from each of said sensors or from a second computer in data communication with each of said sensors, said application also configured to generate, in response to a real-time disposition of each of said corresponding body parts during performance of an exercise related body movement, a virtual reality object viewable by said user, said object being indicative of an additional body movement to be made by said user in order to conform with a user-specific exercise program.

In one embodiment, the system further comprises one or more bio-feedback sensors bodily engaged with said user and in data communication with the first computer or with a processor in data communication with the first computer, each of said one or more bio-feedback sensors configured to output a signal which is indicative of a pain intensity level experienced by the user during performance of the body movement or of the additional body movement and of a level of user-specific impairment. The application is configured to receive inputs from each of the one or more bio-feedback sensors, from the first computer, or from the second computer, said application also configured to generate, in response to a real-time pain intensity level indication during performance of the exercise related body movement that is below a predetermined threshold, a virtual reality object viewable by said user to urge continuance of the exercise related body movement. The present invention is also directed to a system for determining a cervical range of motion, comprising a head harness configured with a plurality of spaced head engageable straps and a superiorly located and substantially horizontally disposed calvarial region from which said plurality of straps extend; a sensor block attached to said calvarial region, said sensor block comprising one or more sensors adapted to detect head movement with respect to a head-related center of rotation in a plurality of translational directions and a plurality of rotational directions, and a processor operable to receive data from said one or more sensors, and to determine, based on said received data, a cervical range of motion which corresponds to displacement of a selected neck region between a starting and ending position; and means for outputting data representative of said determined cervical range of motion.

The present invention is also directed to an automatized method for promoting rehabilitation of neck muscles of a patient suffering from impaired cervical motion, comprising the steps of bodily engaging a head harness provided with one or movement sensors and a processor, said head harness being connected to a head mounted display on which is viewable computer generated images; bodily engaging one or more bio-feedback sensors configured to output to said processor a signal which is indicative of a pain intensity level experienced by the user during performance of a body movement; viewing said images by said display; performing a corresponding head motion that is urged by said generated images; by said processor, determining an ending position for a selected neck region and transmitting, to a computerized device in data communication with said display, signals which are indicative of said ending position and a pain intensity level experienced by said patient at said ending position; and by said computerized device, generating additional images to urge said patient in continuing the head motion beyond said ending position if the pain intensity level thereat is below a predetermined threshold. Brief Description of the Drawings

DETAILED DESCRIPTION

General approach and introduction . . . . The neck therapy device of the present invention is embodied by a head harness applicable to a user-selected and location-specific level of resistance, in accordance with a corrective exercise program developed by a physiotherapist or a trainer. Conformance to the exercise program is facilitated by means of a VR application, which encourages the user to perform head motions during the course of a stimulating interactive activity that optimize rehabilitation of the neck muscles or optimize the workout session. Both the head harness and the virtual reality system are inexpensive, allowing the user to perform the recommended neck exercises in the comfort of one's home.

Figure 1A:
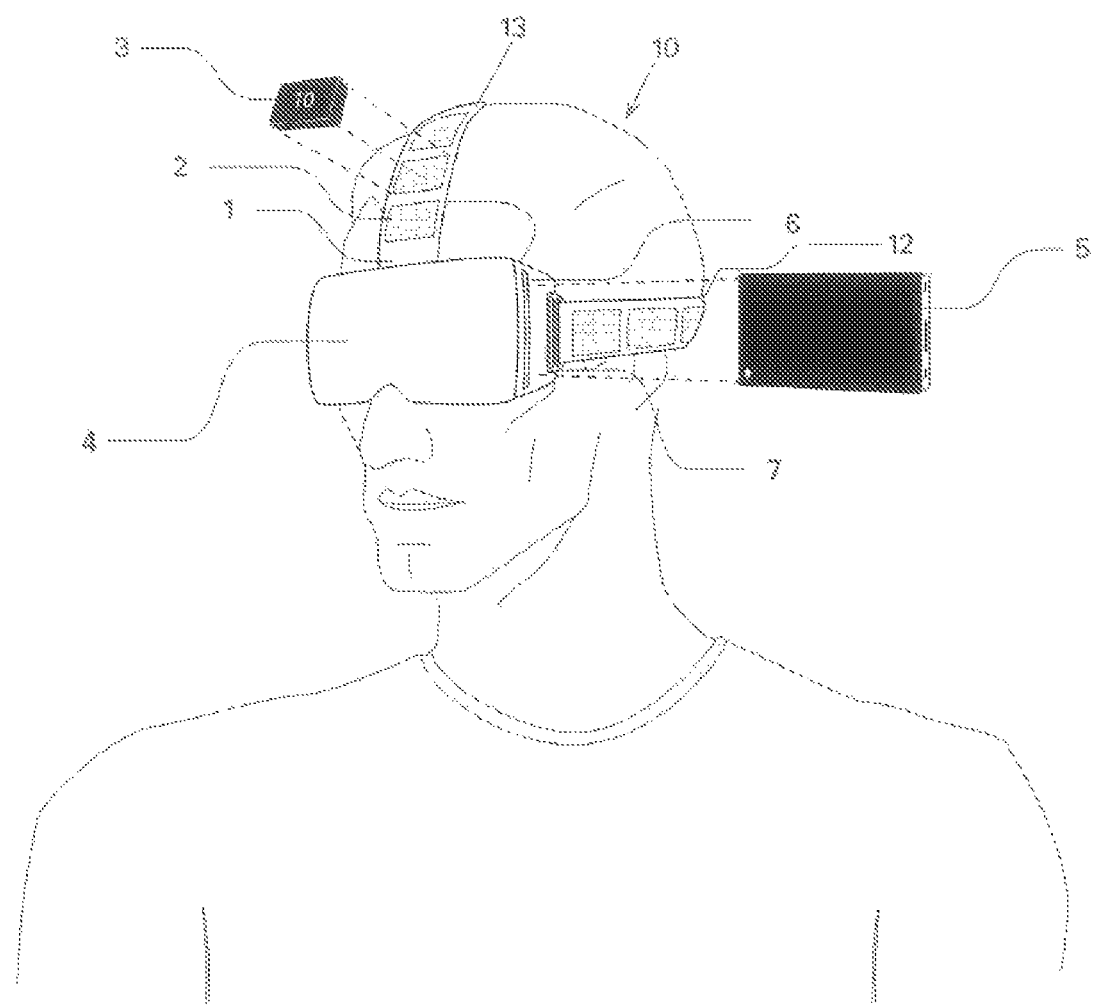
FIG. 1A is a perspective view from the front of a neck therapy device according to one embodiment of the present invention, schematically shown while being assembled.
Figure 1B:
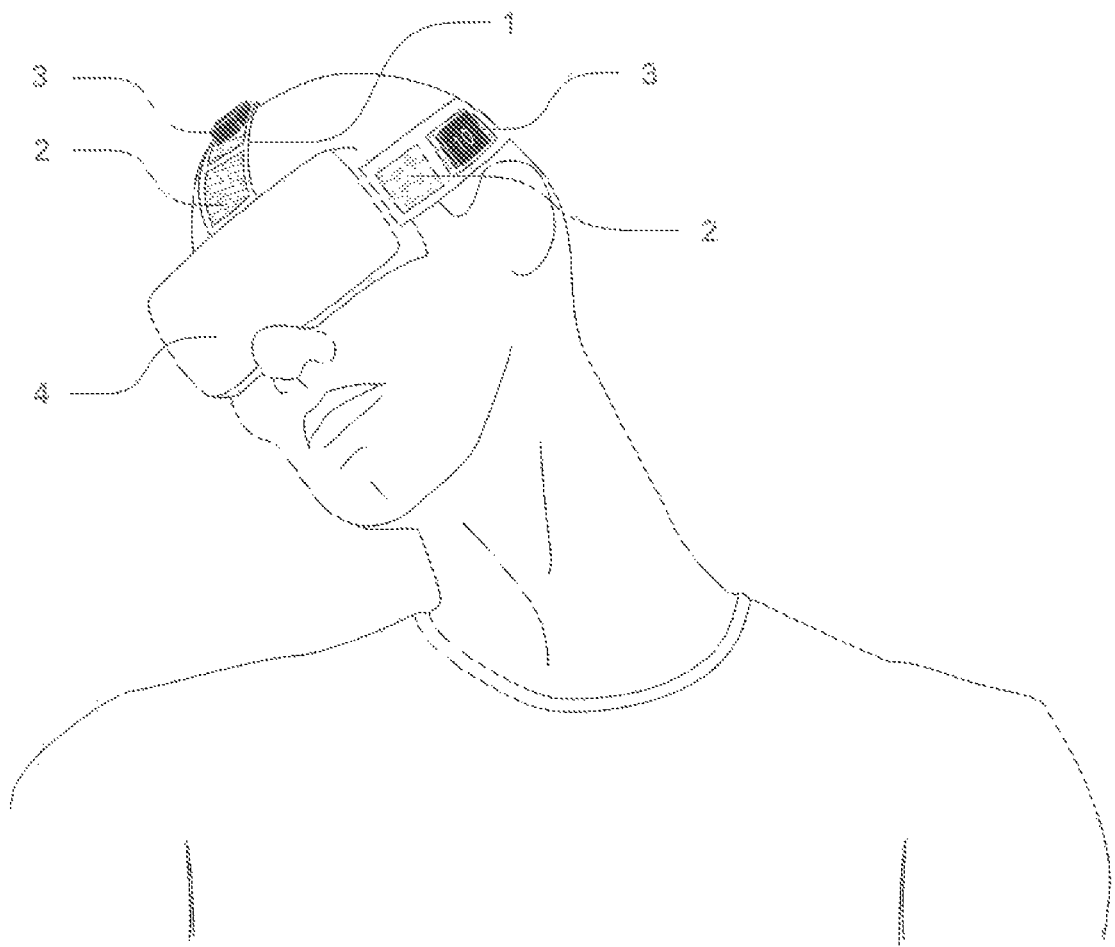
FIG. 1B is a perspective view from the front of the neck therapy device of FIG. 1A, shown after the user with whom it is bodily engaged has undergone a head motion relative to the disposition shown in FIG. 1A.
Figure 1C:
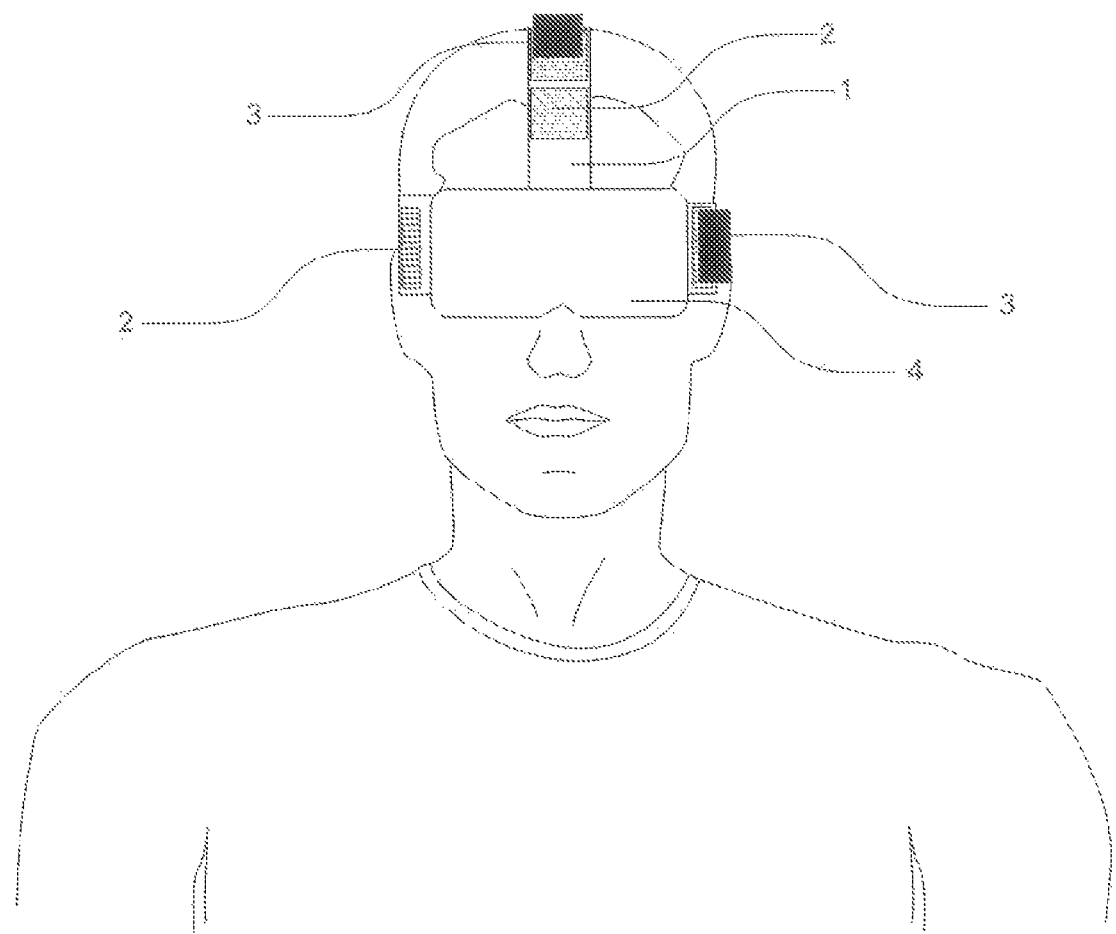
FIG. 1C is a front view of the neck therapy device of FIG. 1A.

FIGS. 1A-C illustrate a first embodiment of the invention wherein neck therapy device 10 comprises a head harness 1 provided with a plurality of spaced patches 2 to each of which a rehabilitative weight 3, e.g. on the order of 10 grams, is removably attachable by hook and loop fastening material, removable adhesive material, snaps, magnets, or other removable fastening means, well known to those skilled in the art, wherein a first fastening element is secured to a patch and a second fastening element for mating with the first, element is secured to a weight.

When magnets are employed, for example, each weight 3 may be embedded e.g. with a neodymium magnet which is covered with an inner lead layer and an outer silicone or fabric layer. A weight 3 is thus attachable to and detachable from a ferrous region formed in a selected patch 2 by means of a magnetic locking system.

Head harness 1 has two straps to which patches 2 are affixed. A first strap 12 encircles the head, when bodily engaged, to define a plane that approximates a transverse plane. A posterior portion of first strap 12 is adapted to engage the back of the head, and right and left anterior portions thereof are secured to a head mounted display (HMD) 4, which may be supported by the nose while being adapted to engage a corresponding side of the head. A second strap 13 substantially perpendicular to first strap 12 is also provided, and is attached to HMD 4 and to a portion of first strap 12 at the back of the head, so that, when bodily engaged, it encircles the skull, to define a plane that approximates a frontal plane while engaging the temporal bone, e.g. the forehead, and the parietal bone. The right and left anterior portions of first strap 12 may be releasably secured to HMD 4 via a corresponding interface member 7.

First strap 12 and second strap 13 may be made of elastomeric material to allow head harness 1 to be mounted on the head or removed by first stretching the straps. Alternatively, they may be made of rigid and non-stretchable material such as a flexible plastic material, e.g. polypropylene or leather and secured to each other by a suitable fastener such as a buckle. Straps 12 and 13 may be cushioned with a pad made of e.g. microfiber fabric or silicone at different locations.

It will be appreciated that head harness 1 may be configured in other ways as well, as long as rehabilitative weights 3 may be removably attached to a patch 2 or any other fastener at a selected region of the skull.

A physiotherapist, or any other medical practitioner, determines the source of the neck pain and develops an exercise program that will optimally provide both rehabilitation and pain relief. The level of resistance is increased when more weights 3 are attached to corresponding patches 2. The weights are attached at patch locations on head harness 1 that will urge the user in response to make a head motion that will strengthen neck muscles that have been found to be weakened. The corrective head motions that can be made with the use of device 10, for example the tilting head motion shown in FIG. 1B, can be selected from flexion when the head is bent forwardly such that the chin is pointing downwardly, extension when the head is bent backwardly such that the chin is pointing upwardly, tilting the head side to side, rotating the head left or right, longitudinal extension or contraction whereby the total length of the neck changes, and any combination thereof. The moment applied by the head in reaction to the application of the weights at a specific head region may be calculated to assist or resist head rotation.

In one aspect, in order to ensure conformance to the exercise program, the user is guided by virtual objects appearing through HMD 4, which is sized to cover the user's eyes and provides a virtual reality display. The HMD is configured to provide depth of perception, such as with a polarized lens at each eye to generate a stereoscopic image. The virtual objects are generated in such a way that, during the course of a stimulating interactive activity, the user is urged to make corrective head motions in accordance with the previously developed exercise program.

In order to make the neck therapy device virtual reality enhanced, the thickened HMD 4 is configured with a slot 6 within which a smartphone 5 is insertable. Smartphone 5, after inserted within slot 6, is substantially parallel to the outer planar surface of HMD 4, such that the display screen of the smartphone faces the eyes of the user while the image forming lenses are interposed between the display screen and the eyes of the user, for example at a distance of 80 mm from the eyes.

An application for providing the virtual reality experience such as a game is running on smartphone 5. The application advantageously receives its inputs from a sensor built in within smartphone 5 that determines the real-time 3-D neck disposition, such as an orientation sensor, gyroscope, accelerometer and geomagnetic field sensor, or a combination thereof. Alternatively, the application receives its inputs from one or more sensors mounted on the head harness. An image is generated by the application and is viewable by the user's eyes in response to the 3-D neck disposition. The user is usually expected in return to make an additional head movement, so that a result programmed according to the rehabilitative needs of the user will be achievable.

For example, the application generates an image that includes a pointer and a target. The spatial distance between the pointer and the target is programmed to ensure user conformance to a given exercise program, when a suitable head movement is subsequently made that will cause the pointer to become aligned with the target.

The application is preferably adapted to cause smartphone 5 to transmit a signal functioning as feedback over a suitable data network to a computerized device with which the physiotherapist interfaces. The transmitted signal may be indicative of the sensor inputs, allowing the physiotherapist to monitor the user's neck motions over time and online, to determine the degree of exercise conformance. The physiotherapist may immediately send data to the application running on the user's smartphone 5 that will override the preprogrammed user-reactive image so that a physiotherapist-selected image will be displayed instead. The physiotherapist-selected image is adapted to urge the user to be in additional conformance with the developed exercise program. If do desired, the physiotherapist-selected image may be one stage of a multi-stage interactive game played between the physiotherapist and user that will encourage the user to achieve optimal exercise compliance at one stage of the game.

As may be appreciated, the use of smartphone 5 as means for real-time tracking and monitoring of head motions and for remote transmission of input signals, in lieu of a dedicated and expensive prior art computer connected VR system, significantly reduces the costs of a virtual reality enhanced neck therapy device. In another aspect, the rehabilitative capabilities of the therapy device may be increased by bodily engaging an external sensor, such as an orientation sensor, to a body part in need of physical therapy, such as an arm or a leg. This external sensor may be in wireless data communication with smartphone 5, by transmitting for example a short range Bluetooth signal to a smartphone transceiver. The application receives the input from the external sensor and generates in response an image viewable on the smartphone screen that allows a result programmed according to the rehabilitative needs of the user to be achieved. The programmed result, for example aligning a pointer with the targeted generated image following a corrective body action, facilitates rehabilitation of the engaged body part, or of a body part proximate thereto.

The image derived from the external sensor may be generated on the smartphone screen in addition to the image derived from the built-in sensor, allowing virtual reality enhanced rehabilitation of the neck as well as of the given body part. Alternatively, a single target image may be displayed on the smartphone screen, to facilitate a programmed result that can be achieved only when both the neck and the given body part perform a corrective action in unison. Alternatively, a single target image may be displayed on the smartphone screen, to facilitate a programmed result that can be achieved by only the given body part.

Figure 2A:
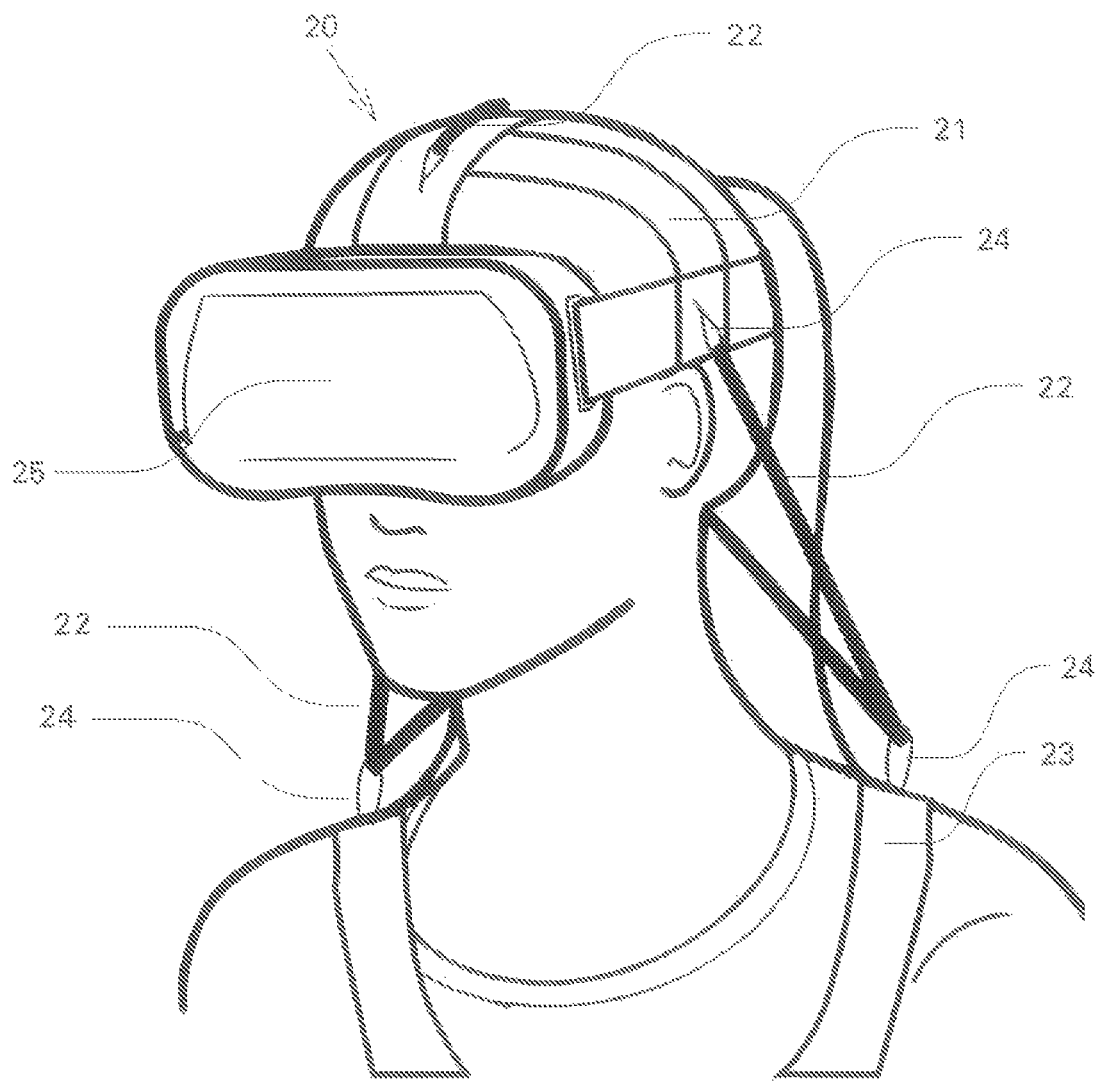
FIG. 2A is a perspective view from the front of a neck therapy device according to another embodiment of the invention.
Figure 2B:
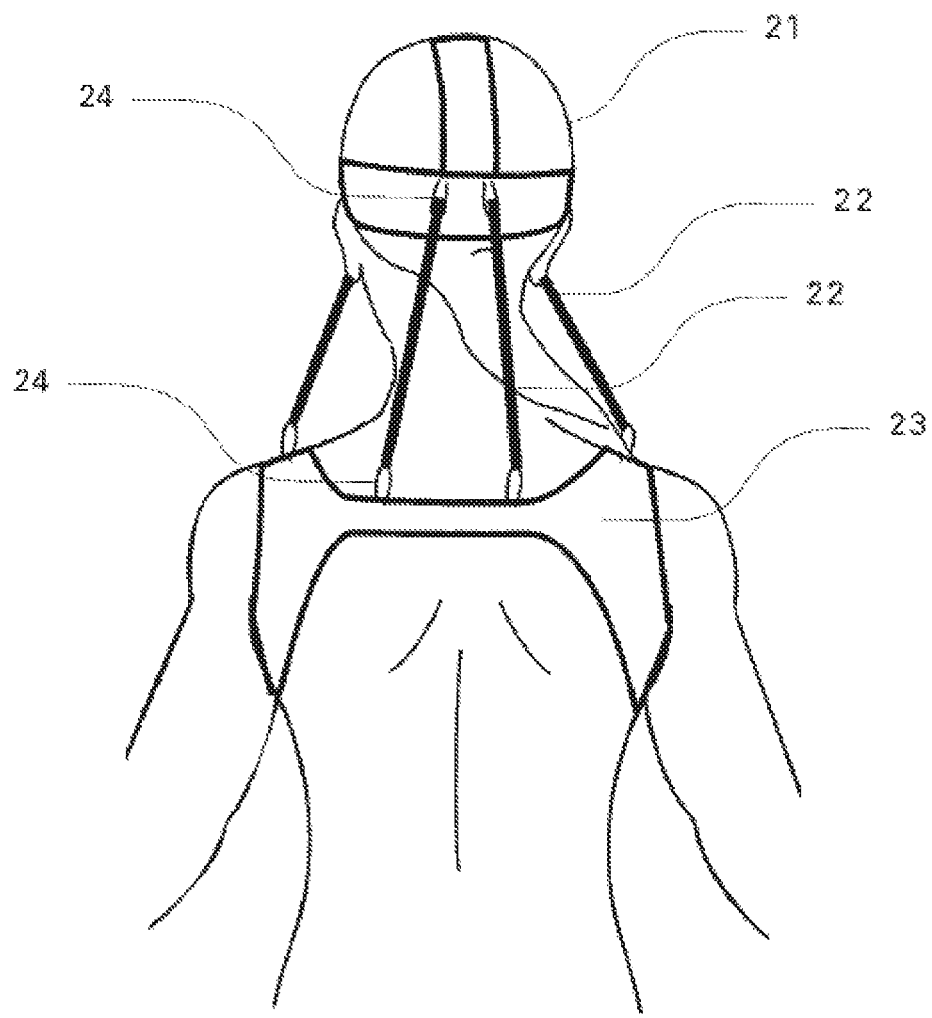
FIG. 2B is a rear view of the neck therapy device of FIG. 2A.

FIGS. 2A-B illustrate a second embodiment of the invention wherein neck therapy device 20 comprises a head harness 21, a body harness 23, a plurality of exchangeable or adjustable resistance cords 22, and HMD 25. Head harness 21 is secured to HMD 25. Both head harness 21 and HMD 25 may be configured similarly to their counterparts in the first embodiment, or alternatively may be configured slightly differently.

A first longitudinal end of each cord 22 is secured to a selected region of head harness 21, and a second longitudinal end of each cord 22 is secured to a selected region of body harness 23. The first and second longitudinal ends of a cord 22 are secured by a corresponding anchoring element 24. An anchoring element 24 in turn is releasably attached to the fabric of head harness 21 or body harness 23 by a clip or the like, or may be permanently attached to the fabric. Alternatively, an end of two or more cords 22 may be secured to a single anchoring element 24. The level of resistance provided by each cord 22 may be adjusted by changing its length. A change in length operation may be carried out by moving the location of an anchoring element 24. If so desired, a first cord having a first length may be exchanged with a second cord having a second length to provide a different resistance. The physiotherapist selects regions of the head to which a predetermined level of resistance is to be applied, in order to develop a user-specific exercise program for providing both rehabilitation and pain relief during performance of a head motion that will strengthen neck muscles that have been found to be weakened.

A smartphone is insertable within HMD 25, to make a rehabilitive activity performable in conjunction with neck therapy device 20 virtual reality enhanced, similarly to neck therapy device 10.

In another embodiment of the invention, the therapy device of the present invention comprises one or more bio-feedback sensors that are adapted to monitor and direct a user during the course of a physical activity.

Figure 3A:
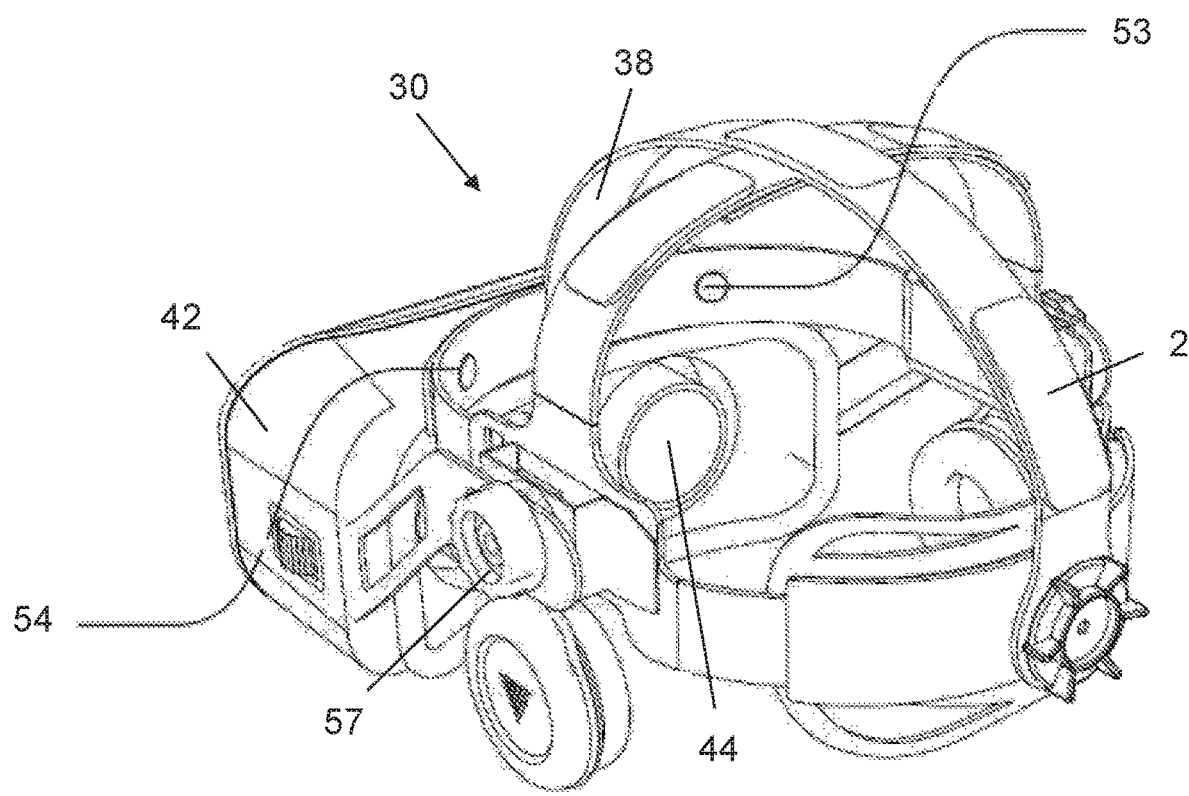
FIG. 3A is a perspective view from the rear of a neck therapy device according to another embodiment of the invention.
Figure 3B:
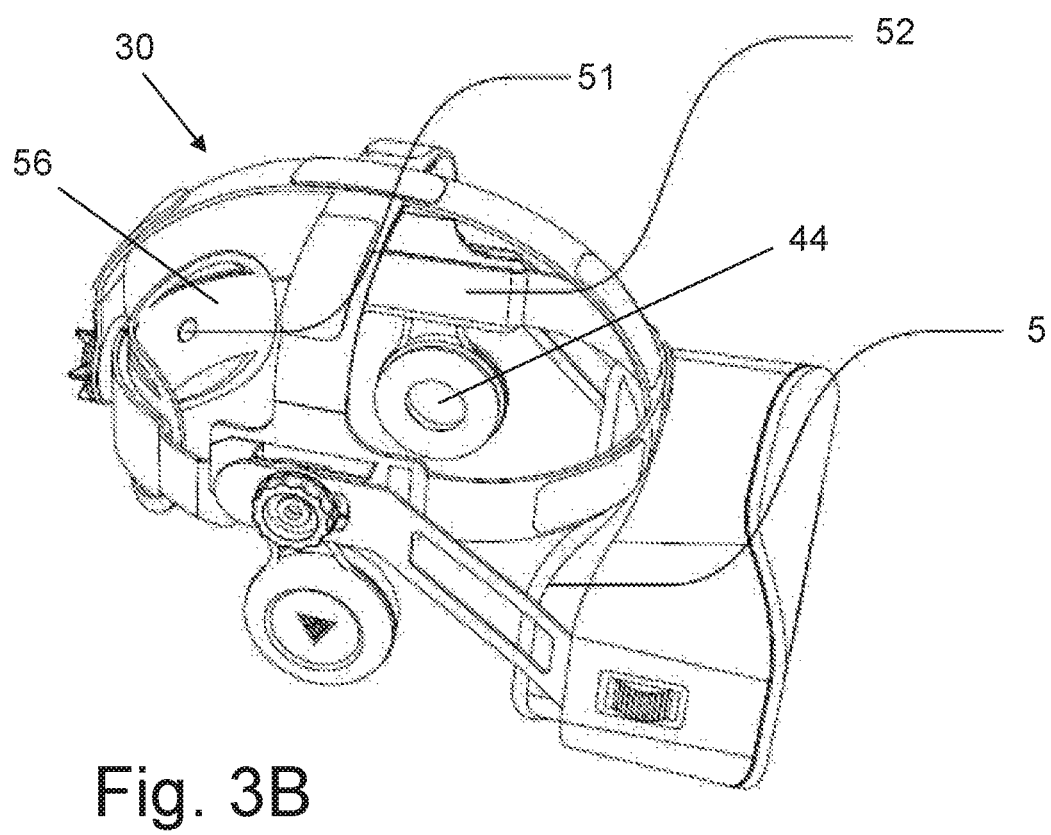
FIG. 3B is a perspective view from the side of the neck therapy device of FIG. 3A.

FIGS. 3A-B illustrate another embodiment of the invention wherein neck therapy device 30 comprises a head harness 38 provided with a plurality of spaced patches 2 to each of which a rehabilitative weight is removably attachable, a HMD 42 in which a smartphone is insertable and which is provided with an optical element 44 for facilitating the virtual reality experience as described hereinabove, and a plurality of bio-feedback sensors. Optical element 44 may be focused by manipulation of one or more dials 57 mounted on the outside of head harness 38 and kinematically connected to a drive unit of the optical element. One bio-feedback sensor may be a heart rate variability (HRV) sensor 52, which is positionable on the inner face of the first strap of head harness 38, so as to contact the palpable superficial temporal artery on side of the forehead. HRV sensor 52, independently or in combination with other bio-feedback sensors, is thus adapted to detect a user reaction to pain by sensing a sudden change in pulse. When sudden pain is detected, for example when the user has achieved a specific 3-D neck disposition, the user becomes aware of the neck region that generates the pain sensation and that needs to be rehabilitated. The bio-feedback sensors may be in wireless data communication with the smartphone, allowing the application to receive in response objective data that is indicative of user performance and that is able to suggest an optimal exercise program, for example by means of images that are viewable by the smartphone screen.

Another bio-feedback sensor may be an electromyography (EMG) sensor 51 for detecting electrical potential produced by the neck muscles during a given activity. EMG sensor 51, which may be provided with a user engageable sensing pad 56, is thus able to measure muscular activity during an exercise program and to transmit the measured data to the application. The exercise program may be automatically modified in response to the received data, or manually changed by user or physiotherapist input. A physiotherapist computer may be connected by a communication link with the application.

A third type of bio-feedback sensor that may be used in conjunction with device 30 is an electroencephalogram (EEG) sensor 54 for detecting electrical activity in the brain of the user during the course of an exercise program. The exercise program may therefore be modified in response to the determined cognitive load of the user, which may be indicative of a suddenly felt pain sensation.

Figure 4:
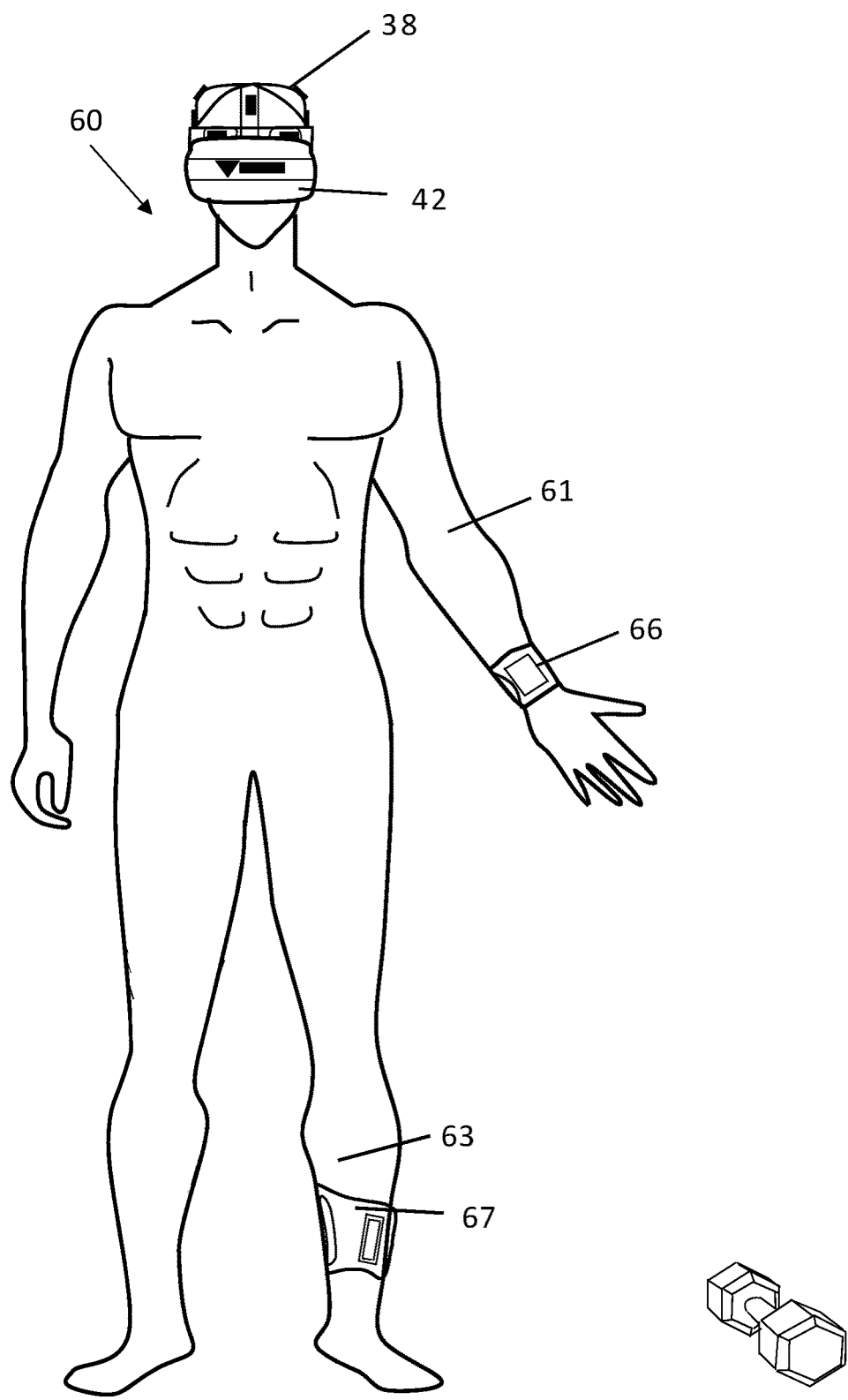
FIG. 4 is a front schematic view of a therapy and physical training system, when bodily mounted, according to an embodiment of the invention.

It will be appreciated that other types of bio-feedback sensors may be used as well, such as a sweat sensor 53. In another embodiment of the invention shown in FIG. 4, physical training system 60 comprises one or more sensors that are positioned on a selected body part, such as an arm 61 or a calf 63. These sensors may be any of the bio-feedback sensors 51-54 illustrated in FIGS. 3A-B, or any other sensors well known to those skilled in the art such as a position or orientation sensor.

A sensor may be placed in proximity to the selected body part by means of a strap, such as an arm strap 66 or a leg strap 67, or by any other well-known fastening means. The strap may be configured with a microcontroller in communication with the sensors, a wireless communication device for transmitting the detected data to the smartphone retained in housing 42, which is connected to head harness 38, and to the application running on the processor of the smartphone, and with a battery pack, e.g. having a capacity of 3.3 V, for powering the sensors.

One or more weights 69 or resistance applying elements well known to those skilled in the art are applied to the vicinity of the selected body part, in order to provide a location-specific level of resistance to a desired body movement that facilitates a given conditioning program. The user views through the optical element of housing 42 one or more virtual reality objects that are suggestive of additional body movements that need to be made by the user in order to conform with the user-specific exercise program. As HMD 42 is connected to head harness 38, the user does not have to hold the smartphone or any other computerized device, allowing the hands to be free to perform an application-recommended exercise.

Figure 5A:
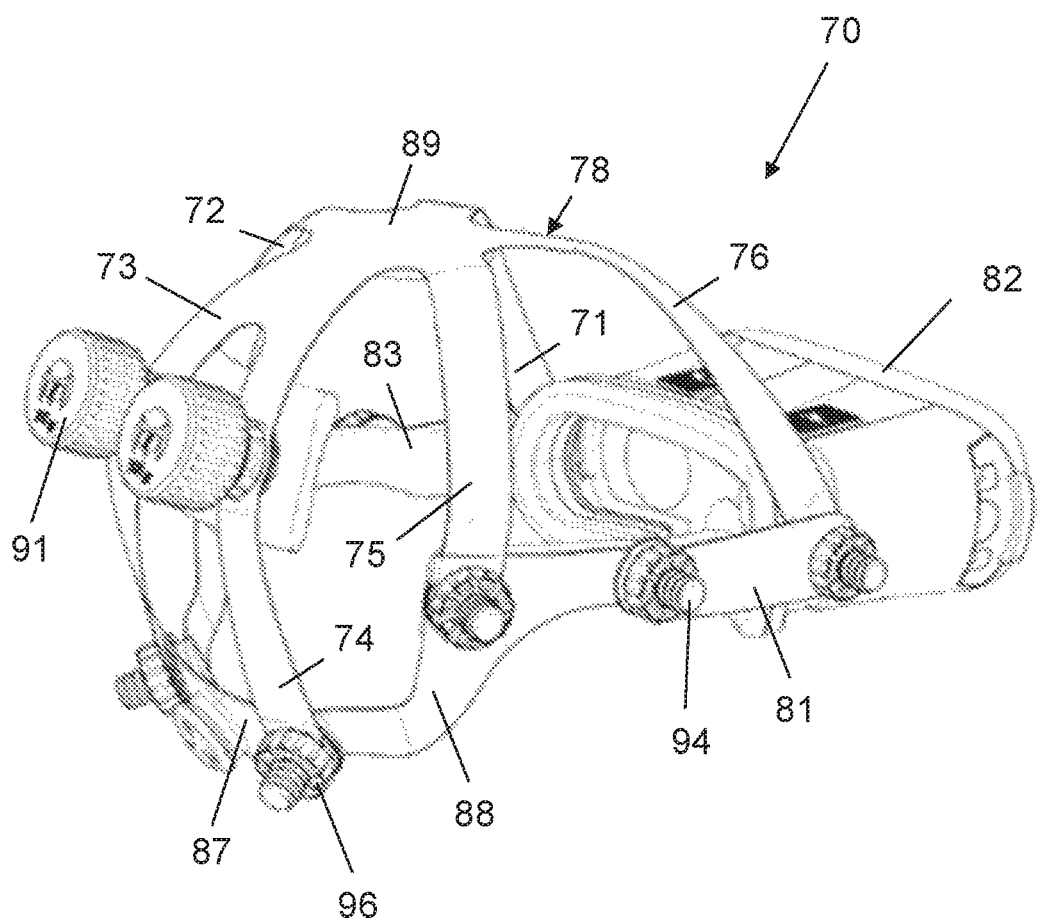
FIG. 5A is a perspective view from the top and side of a neck therapy device according to another embodiment of the invention.

Each weight 69 may comprise a communication device in wireless communication with the smartphone. The application is therefore able to identify each weight 69 and each sensor by a unique identifier and to therefore determine compliance with an exercise program. FIG. 5A illustrates another embodiment of the invention wherein neck therapy device 70 comprises a head harness 78 configured with thin right 81 and left 83 anteroposterior^ extending support sections adapted for engagement with the zygomatic bone, zygomatic process (normally known as the cheek bone) and/or temporal bone, a thin and slightly anteriorly curved occipital support section 87 located inferiorly to anteroposteriorly extending support sections 81 and 83, an interface portion 88 of each anteroposteriorly extending support section having a curved superior and inferior edge to interface with occipital support section 87 at an angle, and a superiorly located and horizontally disposed calvarial region 89 adapted to be fitted on the calvaria, or the substantially flat top of the skull. The anterior end of anteroposteriorly extending support sections 81 and 83 is attached, for example removably attached, to a corresponding lateral end of HMD 82, at a posterior region thereof.

Calvarial region 89 is a junction from which a plurality of straps 71-76, e.g. arcuately shaped straps, extend inferiorly to a support section. Straps 71 and 72 are attached to the anterior and posterior ends, respectively, of support section 83. Straps 75 and 76 are attached to the posterior and anterior ends, respectively, of support section 81. Straps 73 and 74 extending posteriorly along the parietal bone are attached to left and right regions, respectively, of support section 87.

Each of the straps 71-76 is used for positioning a rehabilitative weight at a physiologically important neck-related location. In this embodiment, each rehabilitative weight 91 is threadedly engageable with a corresponding threaded post 94 protruding from a support section or from a strap, to allow a weight 91 to be quickly applied to, or released from, head harness 78. A nut 96 engaged with threaded post 94 may be secured to a support section or strap, such as by adhesion or fusion, or alternatively threaded post 94 may be directly secured to a support section or strap. In order to balance the moment imposed by the weight of HMD 82 about a head-related center or axis of rotation, which may coincide with a known anatomical feature, a relatively heavy weight of at least 150 g, e.g. 300 g, is applied to the junction of support section 87 and straps 73 and 74.

Other weights 91, when applied to a corresponding threaded post 94 at a different head harness region, are used to subject an oppositely located neck related muscle to tension and to thereby induce resistance and muscle growth after that muscle contracts in order to return the head to a balanced equilibrium condition in conjunction with the vestibular system until the head is upright. These other weights may be much lighter, for example ranging from 10-100 g. Of course, the actual applied weight may be varied according to the discretion of the health practitioner in order to conform to a planned exercise program.

A weight applied to a threaded post 94 at both the junction of strap 76 and support section 81 and the junction of strap 71 and support section 83 causes flexion, or a movement by which the chin attempts to touch the chest. Flexion induces resistance at the ilicostalis, longissimus and spinalis muscles that make up the erector spinae, which extends from the lower back of the skull all the way down to the pelvis and assists in bending forward at the waist as well as in promoting the return of the back to the erect position.

A weight applied to one or more of the posteriorly located posts 94 of a single anteroposteriorly extending support section causes rotation of the head in one rotational direction, to induce resistance at the contralateral^ located sternocleidomastoid muscle (SCM) and the group of scalene muscles located in the lateral neck A weight applied to one or more of the centrally located posts 94 of straps 73 and 74 causes extension of the head such that the chin is pointing upwardly, to induce resistance at the longus colli and longus capitis muscles, which are anterior vertebral muscles.

Figure 5B:
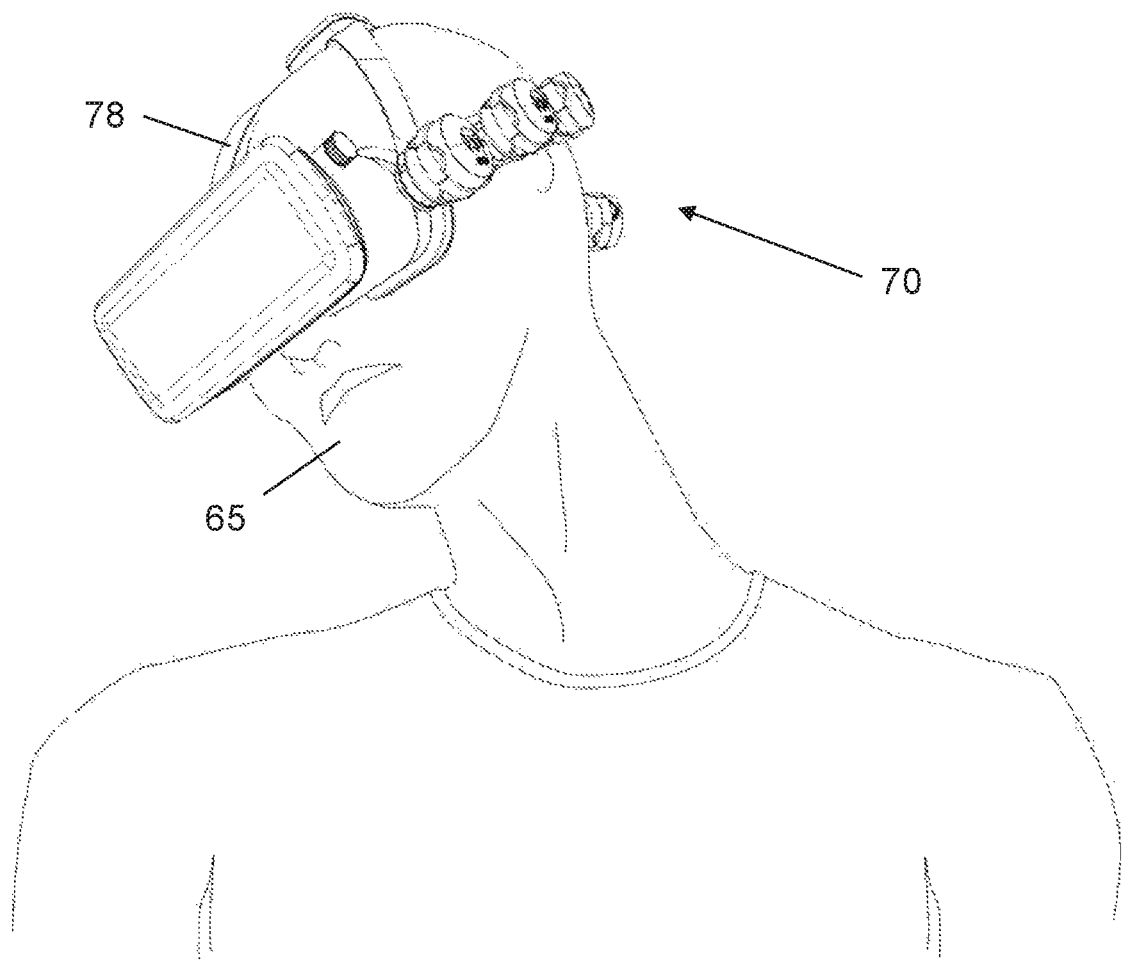
FIG. 5B is a perspective view from the front of the neck therapy device of FIG. 5A, shown after the user with whom it is bodily engaged has undergone a head motion.

FIG. 5B illustrates a user 65 bodily engaged with head harness 78 of neck therapy device 70 who has undergone a lateral flexion movement of the cervical spine by which the neck is tilted in an attempt to touch the ear to the shoulder.

Figure 6:
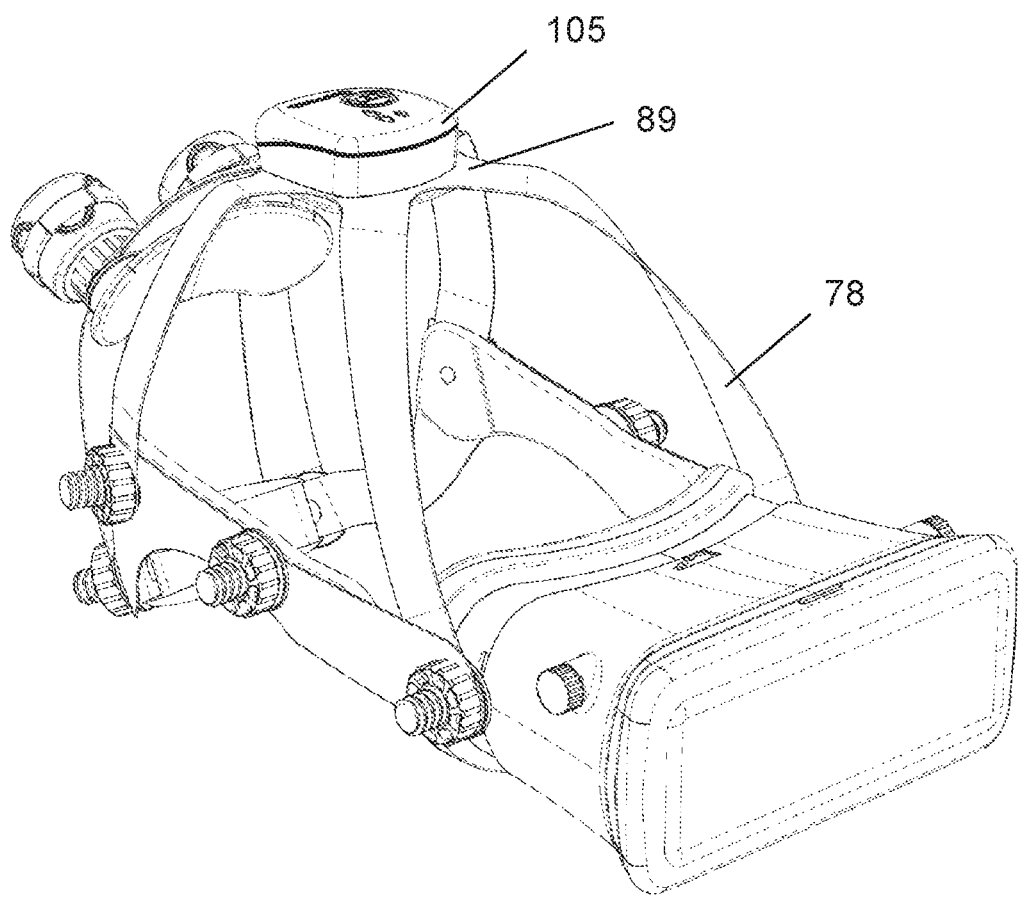
FIG. 6 is a perspective view from the top and front of a neck therapy device according to another embodiment of the invention.

As shown in FIG. 6, calvarial region 89 of head harness 78 is configured to support a sensor block 105 that is positioned thereabove. Sensor block 105 is adapted to detect head movement with respect to the head-related center of rotation in nine directions, six translational directions and three rotational directions. Accelerometers or other types of movement sensors have been found to have a significantly higher level of accuracy when horizontally disposed than when vertically disposed, and therefore the positioning of sensor block 105 on top of the substantially horizontal calvarial region 89 increases the accuracy of head movement measurement.

Figure 7:
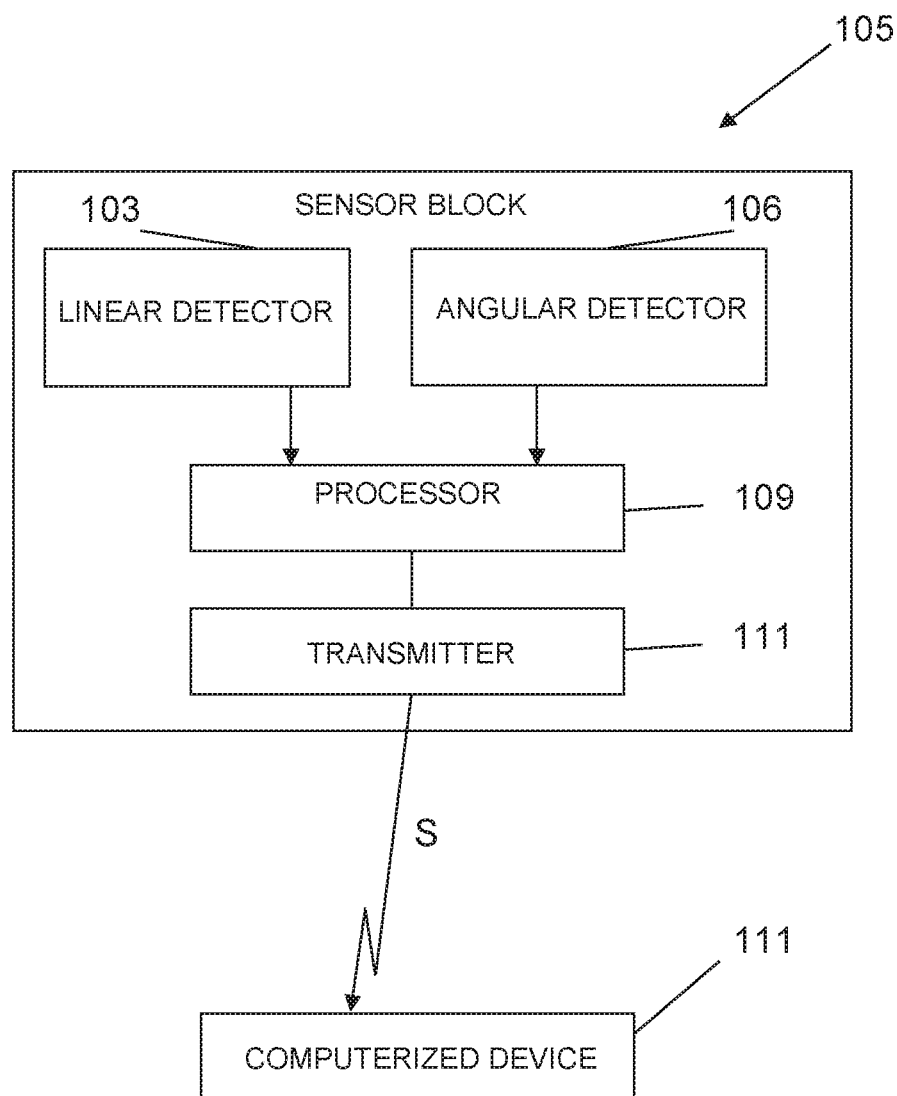
FIG. 7 is a block diagram of a sensor block used in conjunction with the neck therapy device of FIG. 6.

A block diagram of sensor block 105 is shown in FIG. 7. Sensor block 105 comprises a linear motion detector 103 such as an accelerometer for sensing motion along each of the Cartesian axes, and an angular motion detector 106 such as a gyroscope for detecting angular motion about each of the Cartesian axes. If so desired, detectors 103 and 106 may be combined in a single device, such as an inertial measurement unit (IMU). A local processor 107 receives inputs from each of detectors 103 and 106 and determines, based on these inputs and stored instructions, such as by means of the 9-axis algorithm of a motion fusion module, a real-time 3-D neck disposition. A transmitter 109, such as a transceiver, wirelessly transmits the data output by processor 107 via signal S to a computerized device 111, which generates a recommended user-specific action in response to the determined real-time 3-D neck disposition. Transmitter 109 together with the associated communication circuitry may be adapted to transmit a short range signal S or, alternatively, a remote signal via the cellular network or by means of a dongle, for example plugged into a USB port provided with sensor block 105.

When computerized device 111 is a smartphone or any other dedicated processor-enabled mobile device on which the VR application is running and housed within the HMD, the recommended user-specific action is a corrective head motion in response to an application-generated image viewed through the HMD to rehabilitate one or more specific neck muscles. The corrective head motion causes location-specific neck muscles to become tensed by the load imposed by the selectively applied weights and to be then subsequently strengthened.

When computerized device 111 is the computer of a health professional, such as a physiotherapist or a physician, which is connected by a communication link with a local user-accessible computer, for example one housed in the HMD, the corrective head motion is planned by the health professional to take into account an optimal exercise program that supersedes one represented by the application-generated images or that is an originally planned exercise program. Instructions regarding a corrective head motion may be communicated by the microphone or screen of the local user-accessible computer or via the HMD, for example in conjunction with the application.

Figure 8:
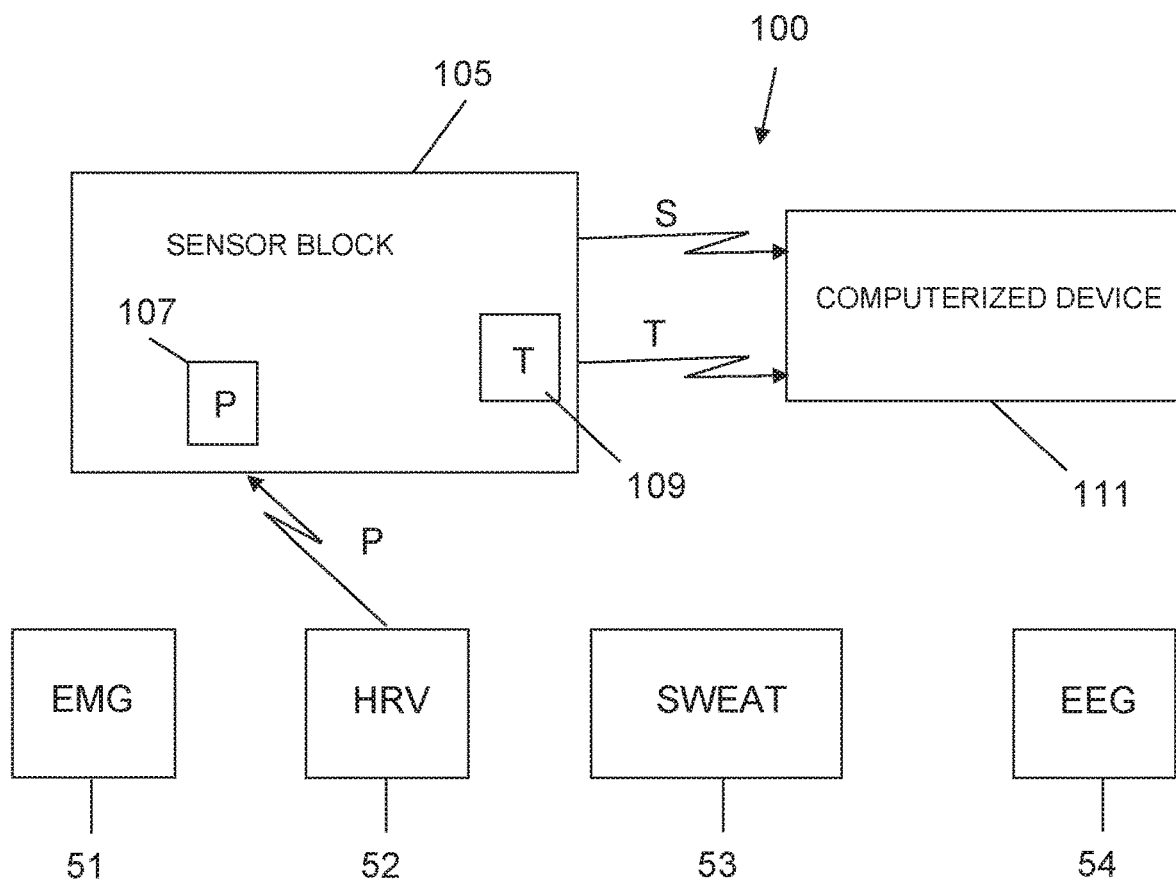
FIG. 8 is a schematic illustration of a system employing the sensor block of FIG. 7 for determining a cervical range of motion.
Figure 9:
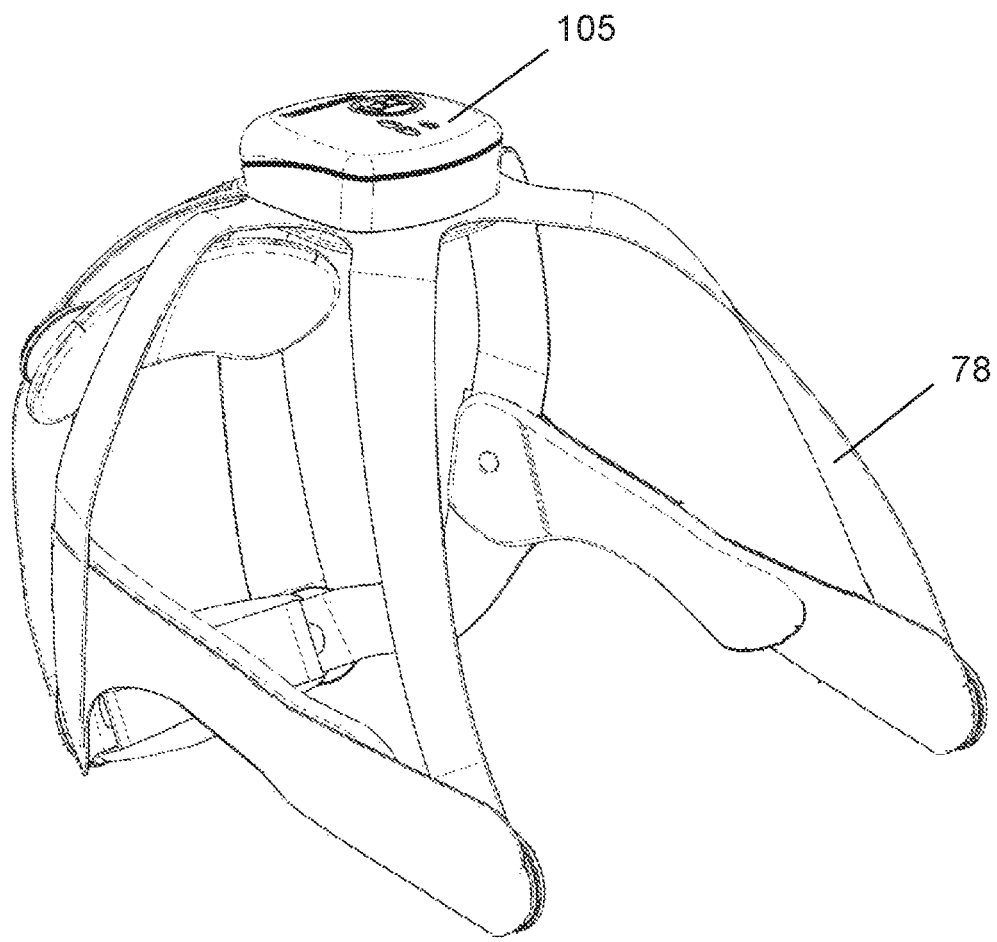
FIG. 9 is a perspective view from the top and front of a neck therapy device according to another embodiment of the invention

Alternatively, computerized device 111 may be a local user-accessible computer that constitutes a PC-based VR platform with a significantly higher level of computer resources and therefore more sophisticated and higher quality image generating capabilities than a processor-enabled mobile device, for use for example in a clinic where user mobility is of less importance. Computerized device 111 is connected to the HMD, which comprises a display and software for interacting with the input from the VR platform, by a wired or a wireless connection. External sensors may be used to track other body parts while head position is HMD derived. As shown in FIG. 8, sensor block 105 may be part of a system 100 used as a diagnostic tool for determining a cervical range of motion (CROM) in conjunction with a head harness 78 shown in FIG. 9 configured without weight coupling means and without a HMD. During the head motion of a user along a curved path or a straight path, processor 107 of sensor block 105 determines the displacement of a selected neck region between a starting and ending position, for example with respect to a physical or virtual reference point, after receiving inputs from each of the linear motion and angular motion detectors. The displacement may be compared with the expected displacement for similar head motion of a healthy person. The expected displacement may be for example the average displacement of a large number of subjects, e.g. 1000 subjects.

CROM assessment for quantifying a level of impairment associated with neck pain is carried out in the prior art by goniometers and inclinometers; however only two-dimensional motion is usually able to be measured with these devices. Electromagnetic motion tracking devices are used to measure three-dimensional motion, but their use is limited due to their cost, technical complexity and requirement to exploit a large amount of computer resources during continuous tracking in real time of the selected neck region. In contrast, the processor of system 100 is programmed to determine only the starting and ending positions. Thus the CROM of the selected neck region is able to be obtained with a minimal load on computer resources to provide a cost effective diagnostic tool, yet with a surprisingly high level of accuracy. The diagnostic tool of the present invention accordingly has much utility to governmental agencies in order to assess levels of disability by determining the CROM.

In addition to the components of sensor block 105 illustrated in FIG. 7, system 100 additionally comprises one or more bio-feedback sensors in wireless or wired data communication with processor 107, such as EMG sensor 51 for detecting electrical potential produced by the neck muscles during a given activity, HRV sensor 52 for detecting a sudden change in pulse, sweat sensor 53 and EEG sensor 54 for detecting electrical activity in the brain. The bio-feedback sensors may be mounted on the head harness or on a suitable body portion. After processor 107 receives a signal P which is indicative of a suddenly detected pain sensation from one or more of these bio-feedback sensors, it transmits a signal S or a signal T to computerized device 111 so that a recommended user-specific action will be generated thereby in response to stored instructions. Signal T is indicative that pain higher than a predetermined intensity level has been sensed, and signal S is representative of the ending neck position or of the total displacement during a given motion when the pain has been sensed. Processor 107 may be previously calibrated to output signal T after the user has been subjected to different types of pain which he or she was able to classify according to different discernable pain intensity levels and each pain intensity level was found to correspond to a measured value of one or more of the bio-feedback sensors.

A transmitter 109, such as a transceiver, wirelessly transmits the data output by processor 107 via signal S to a computerized device 111, which generates a recommended user-specific action in response to the determined real-time CROM. A health practitioner may rely on the indication of the pain intensity level to encourage the patient, i.e. the user on which the head harness is bodily engaged, to continue the cervical motion beyond the user-performed ending position if the indicated pain intensity level is not excessively high.

Figure 10:
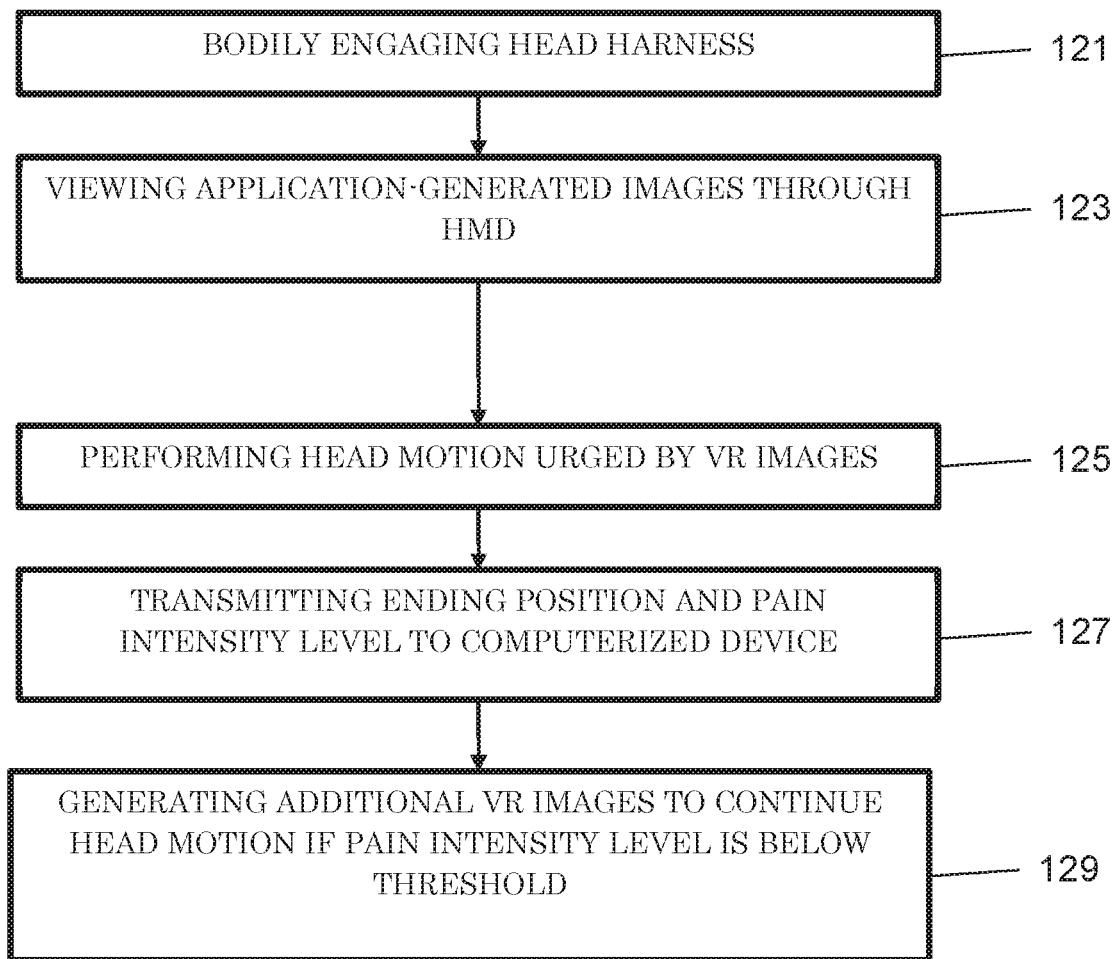
FIG. 10 is a method for automatically rehabilitating a patient suffering from impaired cervical motion.

FIG. 10 illustrates a method for automatically rehabilitating a patient suffering from impaired cervical motion. After the VR-assisted and sensor block mounted head harness is bodily engaged on the patient in step 121, the application generates images in step 123 that are viewed by the patient through the HMD. The patient accordingly performs in step 125 a corresponding head motion that is urged by the generated VR images. The sensor block transmits to the computerized device in step 127 signals which are indicative of the ending position of the head motion and the patient's pain intensity level at the ending position, and the computerized device in turn generates additional images in step 129 to urge the patient in continuing the head motion beyond the previous ending position if the pain intensity level thereat is below a predetermined threshold, as defined by stored instructions.

While some embodiments of the invention have been described by way of illustration, it will be apparent that the invention can be carried out with many modifications, variations and adaptations, and with the use of numerous equivalents or alternative solutions that are within the scope of persons skilled in the art, without exceeding the scope of the claims.

What is claimed is:

1. A system comprising:
   one or more movement sensors each of which are configured to be positioned on a corresponding body part of a user;
   a first computer comprising a processor, a head mounted housing having a display on which images generated by said first computer are visible to said user; and one or more bio-feedback sensors configured to be bodily engaged with said user and in data communication with the first computer or a second computer, wherein said first computer is configured to: i) receive inputs from each of said one or more biofeedback sensors or from the second computer; and ii) generate, in response to a real-time disposition of each of said corresponding body parts during performance of an exercise related body movement, a virtual reality object viewable by said user, said object being indicative of an additional body movement to be made by said user in order to conform with a user-specific exercise program, said one or more bio-feedback sensors are configured to output a signal which is indicative of a pain intensity level experienced by the user during performance of the body movement or of the additional body movement, said one or more movement sensors are configured to output a signal which is indicative of a level of user-specific impairment including a starting position and an ending position from the performance of the body movement or of the additional body movement, said first computer is configured to encourage said user to continue motion beyond the ending position when the signal which is indicative of a pain intensity level experienced by the user during performance of the body movement or of the additional body movement is not above a predetermined intensity.

2. The system of claim 1, wherein the display comprises at least one image forming lens and a slot into which a processor enabled device is inserted.

3. The system of claim 2, wherein the processor enabled device is a smartphone.

4. The system according to claim 1, wherein the first computer is configured to receive inputs from each of the one or more bio-feedback sensors, or from the second computer, the first computer is configured to generate, in response to a real-time pain intensity level indication during performance of the exercise related body movement that is below a predetermined threshold, a virtual reality object viewable by said user to urge continuance of the exercise related body movement.

5. The system of claim 1, wherein the first computer is a personal computer provided with a virtual reality platform and is connected to the head mounted housing.

6. The system of claim 1, wherein the first computer is housed within the head mounted housing.

7. The system of claim 1, wherein the display of the head mounted housing comprises at least one image forming lens through which the virtual reality object is transmittable.

8. The system of claim 1, wherein the computer is configured to determine a displacement based on the starting position and the ending position, and compare said determined displacement to an expected displacement for a similar motion of a healthy person.

9. A method comprising:

bodily engaging a head mounted housing provided with one or movement sensors and a processor, said head mounted housing having a display on which is viewable computer generated images;

bodily engaging one or more bio-feedback sensors, wherein each of said one or more bio-feedback sensors are configured to output to said processor a signal which is indicative of a pain intensity level experienced by the user during performance of a body movement and each of said one or more movement sensors are configured to output a signal which is indicative of a level of user-specific impairment including a starting position and an ending position from a head motion that is urged by said computer generated images;

displaying said images on said display;

by said processor and said one or more movement sensors, determining a starting position and an ending position for a selected neck region and transmitting, to a computerized device in data communication with said display, signals which are indicative of said starting position and said ending position;

by said processor and said one or more bio-feedback sensors, determining a pain intensity level experienced by said patient during the head motion and transmitting, to the computerized device in data communication with said display, signals which are indicative of said pain intensity level; and by said computerized device, generating additional images to urge said patient in continuing the head motion beyond said ending position if the pain intensity level is below a predetermined threshold.

10. The method of claim 9, further comprising:

by said processor, receiving inputs from each of the one or more bio-feedback sensors, from the first computer, or from the second computer;

by said computerized device, generating, in response to a real-time pain intensity level indication during performance of the exercise related body movement that is below a predetermined threshold, a virtual reality object viewable by said user to urge continuance of the exercise related body movement.

11. The method of claim 9, wherein the computerized device comprises a personal computer provided with a virtual reality platform and is operably connected to display to thereby provide the virtual reality platform through the display.

12. The method of claim 9, wherein the computerized device is housed within the head mounted housing.

13. The method of claim 10, wherein the display comprises at least one image forming lens through which the virtual reality object is transmittable.

14. The method of claim 9, wherein the display comprises at least one image forming lens and a slot into which a processor enabled device is inserted.

15. The method of claim 14, wherein the processor enabled device is a smartphone.

* * * * *